US012688730B2

(12) United States Patent
    Kitagawa et al.

(10) Patent No.: US 12,688,730 B2
(45) Date of Patent: Jul. 21, 2026

(54) METHOD, SYSTEM, AND PROGRAM FOR FACIAL EXPRESSION EVALUATION USING REFERENCE AND MEASUREMENT RESULT

(71) Applicant: SHIMADZU CORPORATION, Kyoto (JP)

(72) Inventors: Akane Kitagawa, Kyoto (JP); Koichi Murata, Kyoto (JP); Yasuyuki Uraoka, Kyoto (JP); Masafumi Furuta, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 341 days.

(21) Appl. No.: 18/690,079

(22) PCT Filed: Jul. 8, 2022

(86) PCT No.: PCT/JP2022/027112
    § 371 (c)(1),
    (2) Date: Jul. 1, 2024

(87) PCT Pub. No.: WO2023/037749
    PCT Pub. Date: Mar. 16, 2023

(65) Prior Publication Data
    US 2024/0428617 A1      Dec. 26, 2024

(30) Foreign Application Priority Data
    Sep. 7, 2021      (JP) .................................. 2021-145572

(51) Int. Cl.
    *G06V 40/16*      (2022.01)
    *A61B 5/16*       (2006.01)
    *A61B 5/389*      (2021.01)

(52) U.S. Cl.
    CPC .............. *G06V 40/174* (2022.01); *A61B 5/16* (2013.01); *A61B 5/389* (2021.01); *G06V 40/168* (2022.01); *G06V 40/176* (2022.01); *A61B 5/165* (2013.01)

(58) Field of Classification Search
    CPC ..... G06V 40/16–179; A61B 5/11; A61B 5/16; A61B 5/165; A61B 5/389
    See application file for complete search history.

(56) References Cited

U.S. PATENT DOCUMENTS

| | | | | |
|---|---|---|---|---|
| 2016/0063317 A1* | 3/2016 | Nagai | ................ | G09B 19/0015 |
| | | | | 463/31 |
| 2016/0232561 A1 | 8/2016 | Kikuchi, II et al. | | |

FOREIGN PATENT DOCUMENTS

| | | | | | |
|---|---|---|---|---|---|
| CN | 109730701 B | * | 7/2022 | | |
| CN | 118395387 B | * | 11/2024 | ........... | G06V 40/168 |

(Continued)

OTHER PUBLICATIONS

Notice of Reasons for Refusal dated Nov. 26, 2024 for corresponding Japanese Patent Application No. 2023-546805.

(Continued)

*Primary Examiner* — Scott A Rogers
(74) *Attorney, Agent, or Firm* — Muir Patent Law, PLLC

(57) ABSTRACT

A computer evaluates a facial expression of a subject. More specifically, the computer obtains a reference for physiological information of a facial area of the subject in response to occurrence of a given incident. Further, the computer obtains a measurement result of the physiological information of the facial area of the subject at a targeted timing for evaluation. The computer generates evaluation information about a facial expression of the subject using the reference and the measurement result, and outputs the evaluation information.

13 Claims, 9 Drawing Sheets

(56) References Cited

FOREIGN PATENT DOCUMENTS

| CN | 119693986 | A | * | 3/2025 | |
|----|-----------|---|---|--------|-----|
| CN | 120564235 | A | * | 8/2025 | ............ G10L 25/63 |
| CN | 115240241 | B | * | 9/2025 | ........... A61B 5/0533 |
| CN | 121434860 | A | * | 1/2026 | |
| CN | 121196555 | B | * | 2/2026 | |
| EP | 2982421 | A1 | | 2/2016 | |
| JP | 2005237668 | A | * | 9/2005 | |
| JP | 2008-046691 | A | | 2/2008 | |
| JP | 2014093043 | A | * | 5/2014 | |
| JP | 2017-140198 | A | | 8/2017 | |
| JP | 2018-010305 | A | | 1/2018 | |
| WO | 2015/056742 | A1 | | 4/2015 | |
| WO | 2021/085231 | A1 | | 5/2021 | |

OTHER PUBLICATIONS

Notice of Reasons for Refusal dated Feb. 25, 2025, for corresponding Japanese Patent Application No. 2023-546805.
PCT Written Opinion of the International Searching Authority dated Sep. 27, 2022, for PCT application No. PCT/JP2022/027112.

* cited by examiner

METHOD, SYSTEM, AND PROGRAM FOR FACIAL EXPRESSION EVALUATION USING REFERENCE AND MEASUREMENT RESULT

TECHNICAL FIELD

The present invention relates to a method and system for evaluating a facial expression of a subject, and a non-transitory computer-readable storage medium.

BACKGROUND ART

Human emotions such as comfort and discomfort easily appear in facial expressions, and accordingly, techniques have been proposed for evaluating human expressions in real time. For example, Japanese Patent Laying-Open No. 2018-010305 (PTL 1) discloses a technique of obtaining a facial image of a user (or a subject) who plays a game and scoring an expression of the subject in accordance with a given reference such as a sample image of a smile.

CITATION LIST

Patent Literature

PTL 1: Japanese Patent Laying-Open No. 2018-010305

SUMMARY OF INVENTION

Technical Problem

However, there are individual differences in how an emotion appears in an expression, and it is thus difficult to accurately evaluate an expression of a subject in conventional art.

The present invention has been made in view of the above circumstances, and contemplates a technique for accurately evaluating an expression of a subject.

Solution to Problem

An evaluation method according to an aspect of the present disclosure is a method for evaluating a facial expression of a subject, comprising: obtaining a reference for physiological information of a facial area of the subject; obtaining a measurement result of the physiological information of the facial area of the subject at a targeted timing for evaluation; generating evaluation information about a facial expression of the subject using the reference and the measurement result; and outputting the evaluation information.

An evaluation system according to an aspect of the present disclosure is a system for evaluating a facial expression of a subject, the system comprising a processor and an interface for obtaining physiological information of a facial area of the subject, the processor being configured to generate evaluation information about a facial expression of the subject using a reference for the physiological information of the facial area of the subject and a measurement result of the physiological information of the facial area of the subject obtained at a targeted timing for evaluation, and output the evaluation information.

A non-transitory computer-readable storage medium according to an aspect of the present disclosure is a medium storing a program for causing an evaluation of a facial expression of a subject, the program being executed by a processor of a computer to cause the computer to: obtain a reference for physiological information of a facial area of the subject; obtain a measurement result of the physiological information of the facial area of the subject at a targeted timing for evaluation; generate evaluation information about the facial expression of the subject using the reference and the measurement result; and output the evaluation information.

Advantageous Effects of Invention

In accordance with the present disclosure, a technique is provided for accurately estimating an emotion of an individual.

BRIEF DESCRIPTION OF DRAWINGS

FIG. 4 is a diagram for illustrating generation of evaluation information using emotion indices E1 and E2.

FIG. 7 is a diagram schematically showing a general configuration of an expression evaluation system according to a second embodiment;

DESCRIPTION OF EMBODIMENTS

Hereinafter, embodiments of the present disclosure will be described in detail with reference to the accompanying drawings. In the figures, identical or corresponding components are identically denoted and will not be described repeatedly.

First Embodiment

<System Configuration>

Figure 1:
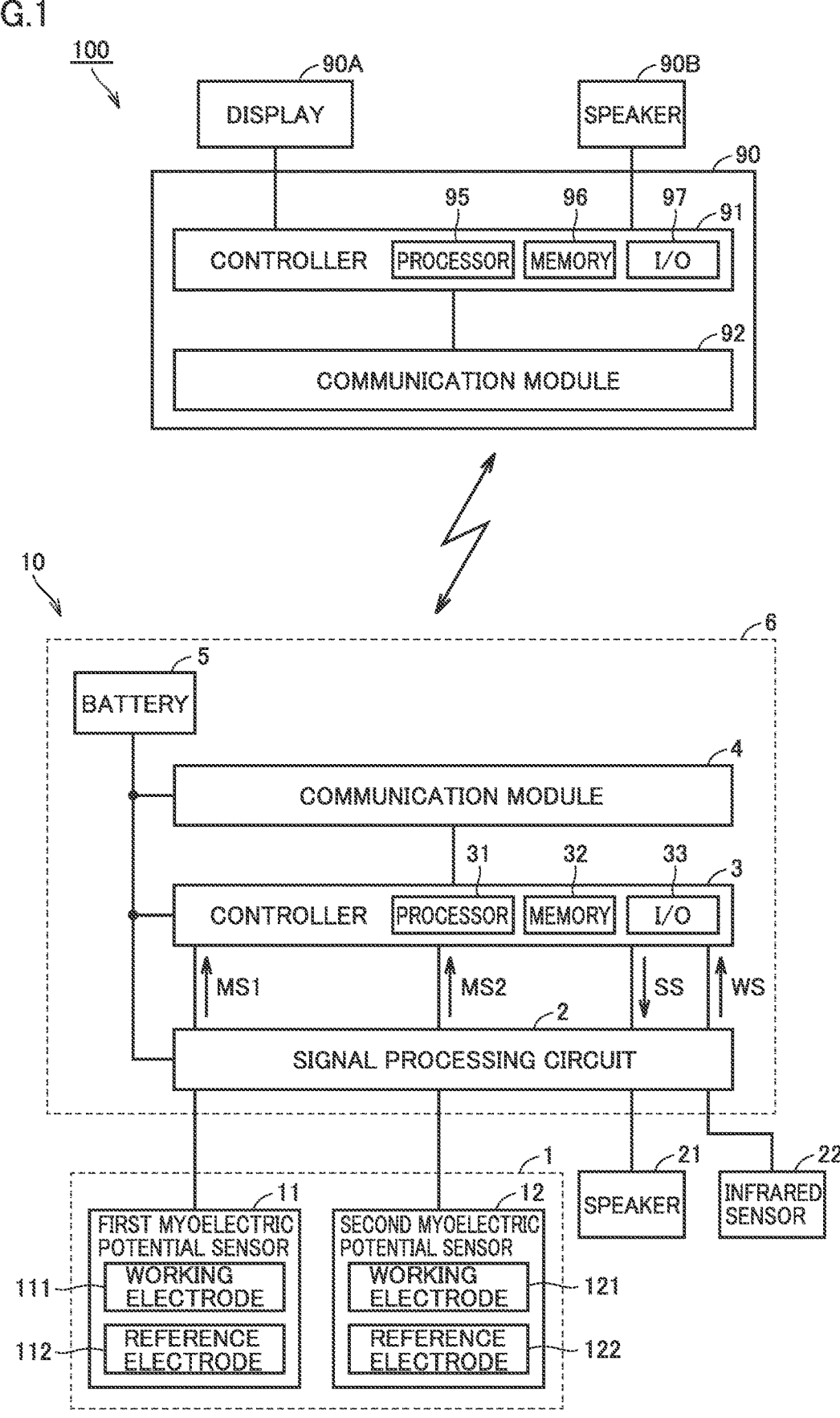
FIG. 1 is a diagram schematically showing a general configuration of an expression evaluation system according to a first embodiment.

FIG. 1 is a diagram schematically showing a general configuration of an expression evaluation system according to a first embodiment. An expression evaluation system 100 shown in FIG. 1 obtains a myoelectric potential signal from a subject, and evaluates an expression of the subject based on a muscular activity represented by the obtained myoelectric potential signal.

Expression evaluation system 100 comprises a wearable terminal 10 and a stationary terminal 90. Wearable terminal 10 is attached to a subject. Stationary terminal 90 is installed in an environment surrounding the subject. Wearable terminal 10 and stationary terminal 90 are configured to be capable of bidirectional communication. Hereinafter, each configuration will be described.

<Wearable Terminal 10>

Wearable terminal 10 includes a sensor unit 1, a signal processing circuit 2, a controller 3, a communication module 4, a battery 5, and a housing 6. Housing 6 houses signal processing circuit 2, controller 3, communication module 4, and battery 5 therein.

Sensor unit 1 includes a first myoelectric potential sensor 11 and a second myoelectric potential sensor 12. First myoelectric potential sensor 11 and/or second myoelectric potential sensor 12 are/is attached to the face of the subject to sense a myoelectric potential signal of a site to which the sensor/sensors is/are attached. In the first embodiment, the myoelectric potential signal is an example of physiological information.

The myoelectric potential signal means a weak electrical signal generated when a muscle is moved. In the present disclosure, a subject's "face" is not limited to the facial region (a front or side surface of the face), and may include the neck of the subject. For example, sensor unit 1 may be attached to the throat of the subject to sense a change in myoelectric potential accompanying a swallowing action of the subject.

Sensor unit 1 may include a plurality of sensors. The plurality of sensors may be attached to different types of muscles. The types of muscles can be identified by sites at which the sensors are attached. In the first embodiment, when a type of muscle is identified, there is no need to identify the muscle in composition or structure. When the sensors are attached to different sites, different types of myoelectric potential signals can be obtained.

Figure 2:
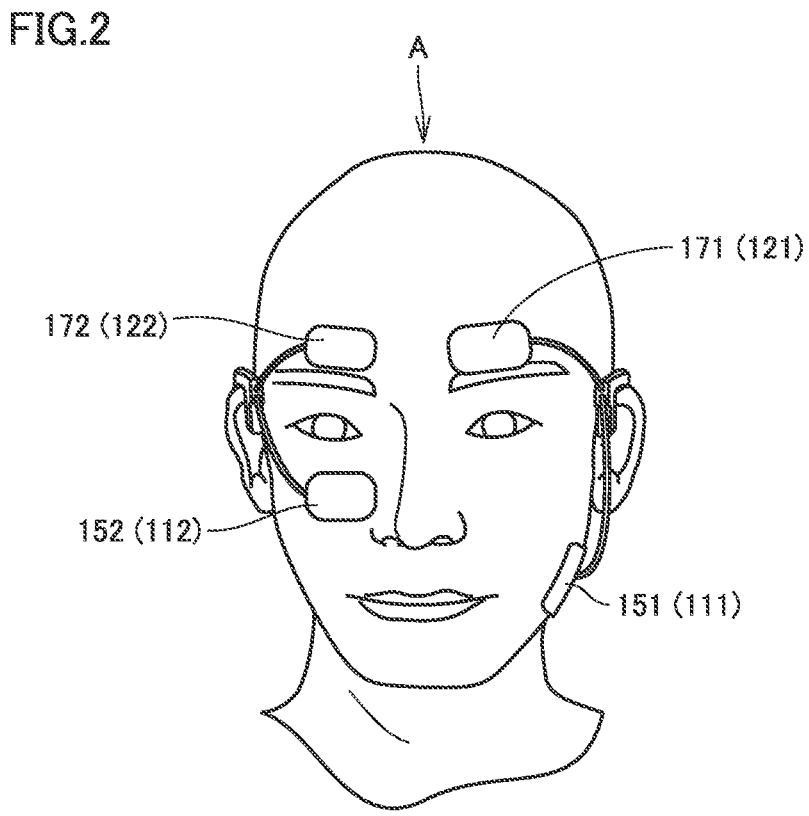
FIG. 2 is a diagram for illustrating attachment sites for a first myoelectric potential sensor 11 and a second myoelectric potential sensor 12 according to the present embodiment.

FIG. 2 is a diagram for illustrating attachment sites for first myoelectric potential sensor 11 and second myoelectric potential sensor 12 according to the present embodiment. With reference to FIG. 2, one aspect in configuration and usage of first myoelectric potential sensor 11 and second myoelectric potential sensor 12 will be described.

First myoelectric potential sensor 11 is attached to the cheeks of the subject. First myoelectric potential sensor 11 includes a working electrode 111 and a reference electrode 112. Working electrode 111 is incorporated in a pad 151, and reference electrode 112 is incorporated in a pad 152.

First myoelectric potential sensor 11 senses a myoelectric potential signal of muscles in vicinities of the cheeks as pad 151 is attached directly on a laughing muscle and pad 152 is attached directly on a zygomaticus major muscle. More specifically, first myoelectric potential sensor 11 senses a potential of working electrode 111 with reference to a potential of reference electrode 112 as a myoelectric potential signal of a muscle in a vicinity of a cheek. Pad 151 and pad 152 (or working electrode 111 and reference electrode 112) may be attached to sites slightly shifted from the laughing muscle and the zygomaticus major muscle, respectively, insofar as the sites are in the vicinities of the muscles. First myoelectric potential sensor 11 outputs the myoelectric potential signals to signal processing circuit 2 of wearable terminal 10 as myoelectric potential signals indicating activities of facial muscles of the portions of the cheeks.

Second myoelectric potential sensor 12 is attached to the eyebrows of the subject. Second myoelectric potential sensor 12 includes a working electrode 121 and a reference electrode 122. Working electrode 121 is incorporated in a pad 171, and reference electrode 122 is incorporated in a pad 172.

Second myoelectric potential sensor 12 senses a myoelectric potential signal of a muscle in a vicinity of an eyebrow (for example, a corrugator supercilii muscle) as pad 171 and pad 172 are attached immediately above corrugator supercilii muscles. More specifically, second myoelectric potential sensor 12 senses a potential of working electrode 121 with reference to a potential of reference electrode 122 as a myoelectric potential signal of a muscle in a vicinity of an eyebrow. Pad 171 and pad 172 (or working electrode 121 and reference electrode 122) may be attached to sites slightly shifted from immediately above the corrugator supercilii muscles insofar as the sites are in the vicinities of the corrugator supercilii muscles. Second myoelectric potential sensor 12 outputs the myoelectric potential signals to signal processing circuit 2 as myoelectric potential signals indicating activities of the corrugator supercilii muscles.

In the example of FIG. 2, the laughing, zygomaticus major, and corrugator supercilii muscles are examples of facial muscles. More specifically, the laughing and zygomaticus major muscles are examples of muscles in a vicinity of a cheek. The corrugator supercilii muscle is an example of a muscle in a vicinity of an eyebrow.

Referring again to FIG. 1, wearable terminal 10 further includes controller 3. Although not shown in the figure, signal processing circuit 2 includes a filter, an amplifier, and an A/D converter. Signal processing circuit 2 applies predetermined signal processing (noise removal, rectification, amplification, digitization, etc.) to each myoelectric potential signal obtained from sensor unit 1 and outputs each processed signal to controller 3.

In FIG. 1, a signal received from first myoelectric potential sensor 11 and processed by signal processing circuit 2 is referred to as a "myoelectric potential signal MS1," and a signal received from second myoelectric potential sensor 12 and processed by signal processing circuit 2 is referred to as a "myoelectric potential signal MS2."

Controller 3 is a computing device including a processor 31, a memory 32, and an input/output port 33. Processor 31 is implemented for example by a CPU (a central processing unit). Memory 32 is implemented for example by a ROM (read only memory) and a RAM (random access memory). Input/output port 33 is an interface in controller 3 for inputting/outputting data. Controller 3 performs a computing process for evaluating an expression of a subject based on myoelectric potential signals MS1 and MS2.

Wearable terminal 10 further includes communication module 4. Communication module 4 causes wearable terminal 10 to communicate with an external device, and is implemented for example by a communication device conforming to a short-range wireless communication standard. Controller 3 controls communication module 4 to control communication of information between wearable terminal 10 and outside (such as stationary terminal 90).

Wearable terminal 10 further includes battery 5. Battery 5 is a secondary battery such as a lithium ion secondary battery. Battery 5 supplies an operating voltage to each component in wearable terminal 10.

Wearable terminal 10 further includes a speaker 21 and an infrared sensor 22. Controller 3 outputs a control signal (a "signal SS" in FIG. 1) to speaker 21 to provide an audio output through speaker 21. Further, controller 3 determines whether wearable terminal 10 is attached to a person based on an output of sensing by infrared sensor 22 (a "signal WS" in FIG. 1).

<Stationary Terminal 90>

Stationary terminal 90 is, for example, a personal computer (PC) or a server. Stationary terminal 90 communicates with wearable terminal 10 via a communication module (not shown) and receives a signal indicating a computation result of controller 3. Stationary terminal 90 includes a controller 91 and a communication module 92.

As well as controller 3, controller 91 includes a processor 95, a memory 96, and an input/output port 97, and executes a variety of computing processes. As well as communication module 4, communication module 92 is implemented for example by a communication device conforming to a short-range wireless communication standard. That is, communication module 92 causes stationary terminal 90 to communicate with another device.

Controller 91 is connected to a display 90A and a speaker 90B. Controller 91 displays a screen that is a computation result on display 90A, and provides an audio output that is a computation result via speaker 90B.

<Structure of Wearable Terminal 10>

Figure 3:
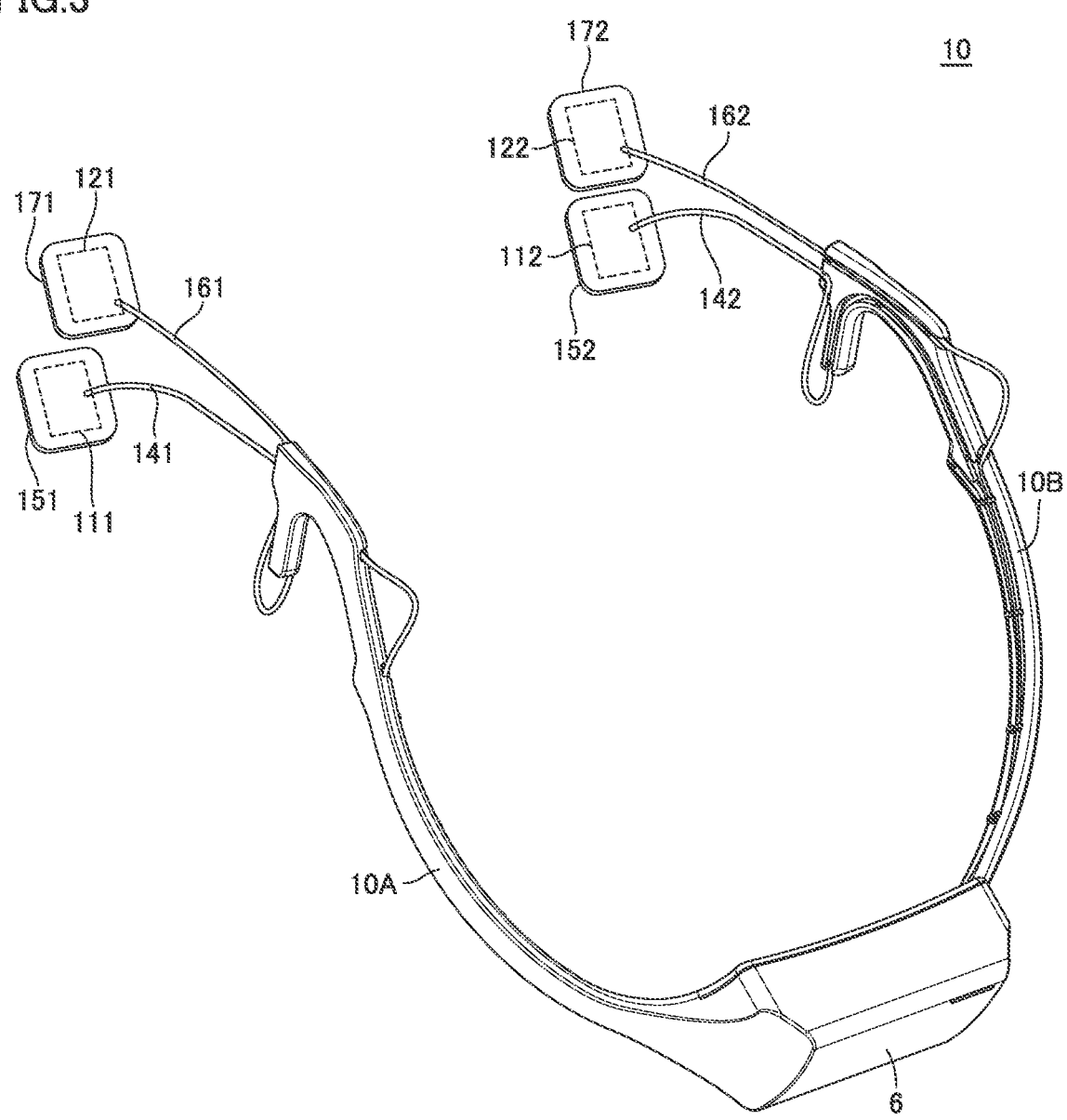
FIG. 3 is a diagram schematically showing a structure of a wearable terminal 10.

FIG. 3 is a diagram schematically showing a structure of wearable terminal 10. As shown in FIG. 3, wearable terminal 10 has an outer shell mainly composed of housing 6. Housing 6 includes a first arm 10A and a second arm 10B.

Housing 6 accommodates a variety of types of elements including signal processing circuit 2 (see FIG. 1). Signal processing circuit 2 and first myoelectric potential sensor 11 (or working electrode 111 and reference electrode 112) are connected by lines 141 and 142. Signal processing circuit 2 and second myoelectric potential sensor 12 (or working electrode 121 and reference electrode 122) are connected by lines 161 and 162.

Speaker 21 and infrared sensor 22 (see FIG. 1) are installed for example at first arm 10A and/or second arm 10B. When wearable terminal 10 is attached to the head of a subject (see FIG. 2), infrared sensor 22 senses infrared radiation from the subject.

<Emotion Index>

In general, it is believed that an emotion of discomfort appears in an activity of a muscle in a vicinity of an eyebrow, as an expression when it is unpleasant or there is a concern is represented as "eyebrows angled." In contrast, it is believed that an emotion of comfort appears in an activity of a muscle in a vicinity of a cheek, as an expression when feeling happy or relieved is represented as "cheeks loosen." By monitoring the activities of these muscles, expression evaluation system 100 generates information to be used for evaluation of expressions of a subject.

Emotion indices E1 and E2 are an example of information generated for evaluation of expressions. Emotion indices E1 and E2 are calculated according to the following equations (1) and (2), respectively.

$$E1 = k11 \cdot A1 + k12 \cdot A2 \tag{1}$$

$$E2 = k21 \cdot A1 + k22 \cdot A2 \tag{2}$$

In the equations (1) and (2), A1 represents an activity value of a muscle in a vicinity of a cheek. A2 represents an activity value of a muscle in a vicinity of an eyebrow. k11, k12, k21, and k22 each represent a previously prepared count. That is, emotion index E1 is calculated by adding a product of activity value A1 and coefficient k11 and a product of activity value A2 and coefficient k12 together. Emotion index E2 is calculated by adding a product of activity value A1 and coefficient k21 and a product of activity value A2 and coefficient k22 together.

In one implementation, activity value A1 of the muscle in the vicinity of the cheek is determined as a sum in potential of working electrode 111 with reference to a potential of reference electrode 112 for a given period of time. Furthermore, in one implementation, activity value A2 of the muscle in the vicinity of the eyebrow is determined as a sum in potential of working electrode 121 with reference to a potential of reference electrode 122 for a given period of time. Emotion index E1 may be an indicator indicating a positive emotion in strength, and emotion index E2 may be an indicator indicating a negative emotion in strength.

<Evaluation Information>

Figure 4:
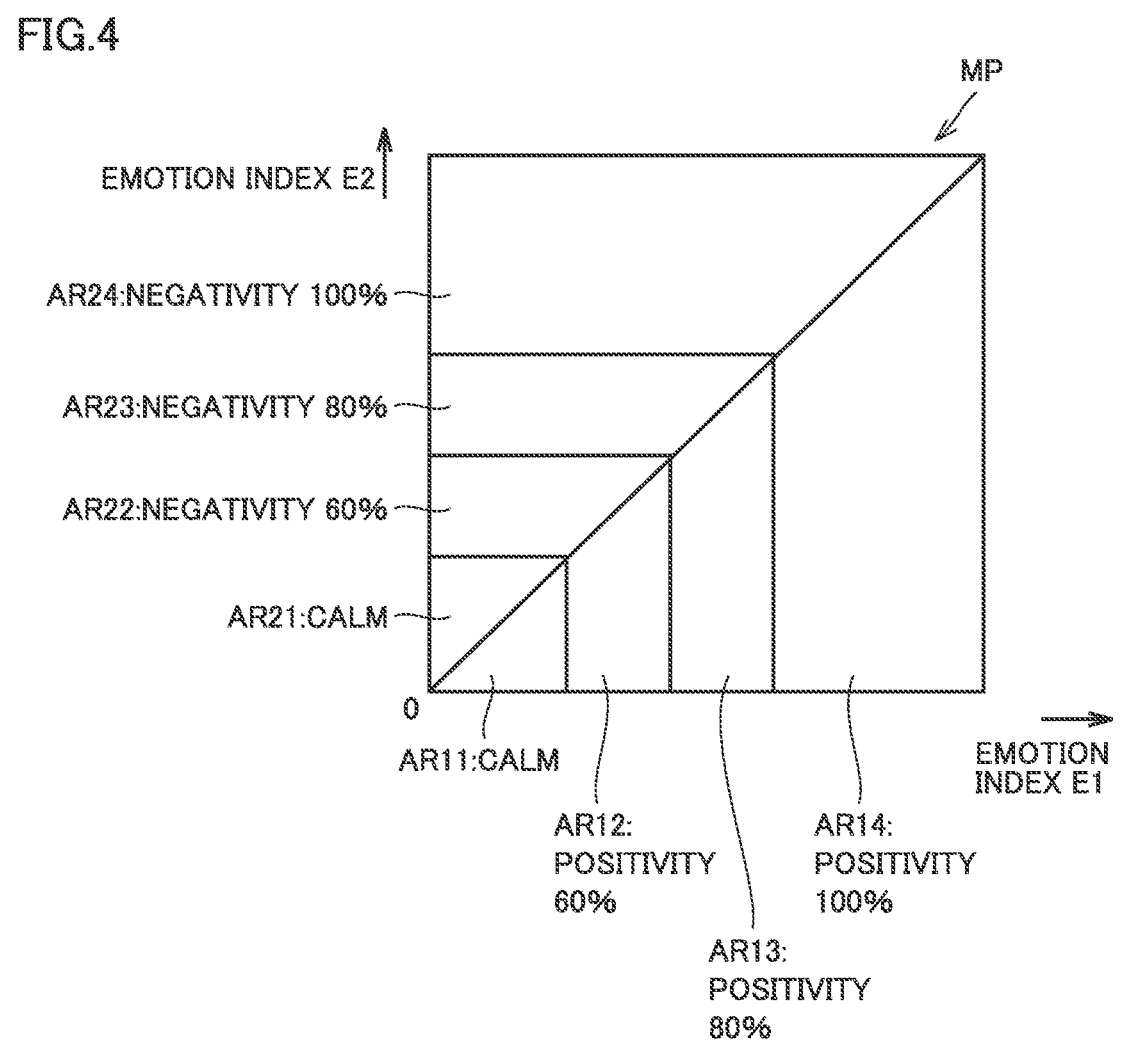

Expression evaluation system 100 generates evaluation information about an expression of a subject using emotion indices E1 and E2 described above. FIG. 4 is a diagram for illustrating generation of evaluation information using emotion indices E1 and E2.

FIG. 4 shows a map MP. In map MP, the abscissa represents emotion index E1, and the ordinate represents emotion index E2. Map MP includes eight regions, that is, regions AR11 to AR14 and regions AR21 to AR24. Regions AR11 to AR14 correspond to evaluation information "calm," a "positivity of 60%," a "positivity of 80%" and a "positivity of 100%," respectively. Regions AR21 to AR24 correspond to evaluation information "calm," a "negativity of 60%," a "negativity of 80%" and a "negativity of 100%," respectively.

In the first embodiment, a combination of emotion index E1 and emotion index E2 is determined, one of regions AR11 to AR14 and AR21 to AR24 corresponding to the determined combination is determined, and evaluation information corresponding to the determined region is determined to generate (or determine) evaluation information corresponding to emotion indices E1 and E2.

<Flow of Process>

Figure 5:
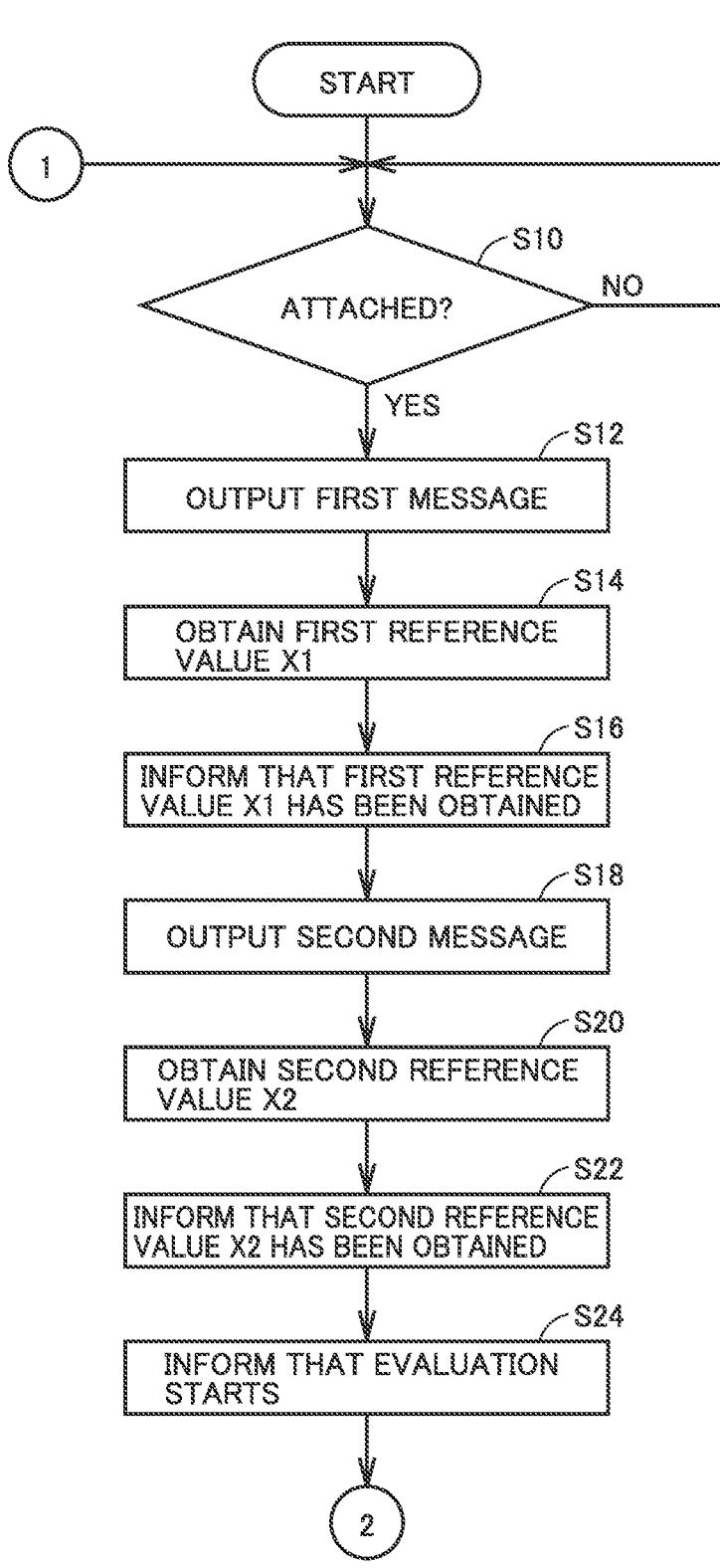
FIG. 5 is a flowchart of a process performed in an expression evaluation system 100 by a stationary terminal 90 to output evaluation information.
Figure 6:
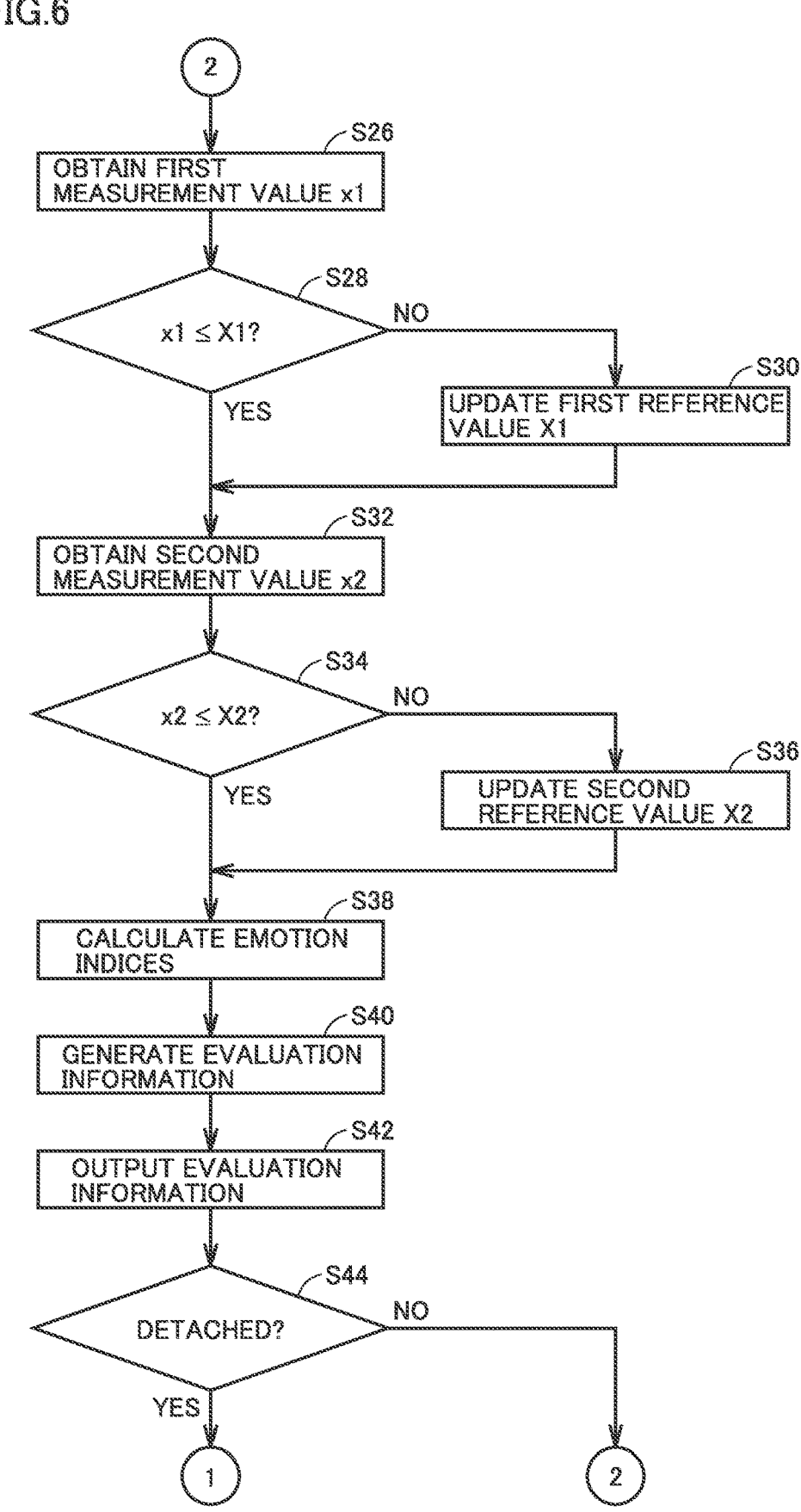
FIG. 6 is a flowchart of a process performed in expression evaluation system 100 by stationary terminal 90 to output evaluation information.

FIGS. 5 and 6 are a flowchart of a process performed in expression evaluation system 100 by stationary terminal 90 to output evaluation information. In one implementation, at stationary terminal 90, processor 95 executes a given program to perform this process. The flow of the process will be described with reference to FIGS. 5 and 6.

Initially, referring to FIG. 5, in step S10, stationary terminal 90 determines whether wearable terminal 10 is attached to a subject. In one implementation, stationary terminal 90 determines whether wearable terminal 10 is attached to the subject based on whether a sensed signal from infrared sensor 22 provided at first arm 10A and/or second arm 10B indicates that wearable terminal 10 is attached to the head of the subject.

Stationary terminal 90 repeats step S10 until it determines that wearable terminal 10 is attached to the subject (NO in step S10). When stationary terminal 90 determines that wearable terminal 10 is attached to the subject (YES in step S10), stationary terminal 90 proceeds to step S12.

In step S12, stationary terminal 90 outputs a first message. The first message is a message that urges the subject to create a positive expression. In one implementation, stationary terminal 90 provides an audio output "Please smile" via speaker 21.

In step S14, stationary terminal 90 obtains a first reference value X1. First reference value X1 is a reference value for an activity value of a muscle in a vicinity of a cheek. In one implementation, stationary terminal 90 obtains, as first reference value X1, a sum in potential of working electrode 111 with reference to a potential of reference electrode 112 for a given period of time. Then, stationary terminal 90 stores first reference value X1 in memory 96.

In step S16, stationary terminal 90 informs that first reference value X1 has been obtained. In one implementation, stationary terminal 90 provides an audio output "First reference value X1 has been obtained." via speaker 21 in step S16.

In step S18, stationary terminal 90 outputs a second message. The second message is a message that urges the subject to create a negative expression. In one implementation, stationary terminal 90 provides an audio output "Please frown." via speaker 21.

In step S20, stationary terminal 90 obtains a second reference value X2. Second reference value X2 is a reference value for an activity value of a muscle in a vicinity of an eyebrow. In one implementation, stationary terminal 90 obtains, as second reference value X2, a sum in potential of working electrode 121 with reference to a potential of reference electrode 122 for a given period of time. Then, stationary terminal 90 stores second reference value X2 in memory 96.

In step S22, stationary terminal 90 informs that second reference value X2 has been obtained. In one implementation, stationary terminal 90 provides an audio output "Second reference value X2 has been obtained." via speaker 21 in step S22.

In step S24, stationary terminal 90 informs that an evaluation of an expression of the subject starts. In one implementation, stationary terminal 90 provides an audio output "Evaluation starts." via speaker 21 in step S24.

Referring to FIG. 6, in step S26, stationary terminal 90 obtains a first measurement value x1. First measurement value x1 is an activity value of the muscle in the vicinity of the cheek. In one implementation, stationary terminal 90 obtains a sum in potential of working electrode 111 with reference to a potential of reference electrode 112 for a given period of time after step S24. Then, stationary terminal 90 obtains the sum as first measurement value x1 and stores it in memory 96. The "given period of time" for which first measurement value x1 is obtained is an example of timing targeted for evaluation.

In step S28, stationary terminal 90 determines whether first measurement value x1 is equal to or smaller than first reference value X1. When stationary terminal 90 determines that first measurement value x1 is equal to or smaller than first reference value X1 (YES in step S28), stationary terminal 90 proceeds to step S32. When stationary terminal 90 determines that first measurement value x1 is not equal to or smaller than first reference value X1 (NO in step S28), stationary terminal 90 proceeds to step S30.

In step S30, stationary terminal 90 updates the value of first reference value X1 stored in memory 96 with the value of first measurement value x1, and proceeds to step S32.

In step S32, stationary terminal 90 obtains a second measurement value x2. Second measurement value x2 is an activity value of the muscle in the vicinity of the eyebrow. In one implementation, stationary terminal 90 obtains a sum in potential of working electrode 121 with reference to the potential of reference electrode 122 for a given period of time after step S24. Then, stationary terminal 90 obtains the sum as second measurement value x2 and stores it in memory 96. The "given period of time" for which second measurement value x2 is obtained is an example of timing targeted for evaluation.

In step S34, stationary terminal 90 determines whether second measurement value x2 is equal to or smaller than second reference value X2. When stationary terminal 90 determines that second measurement value x2 is equal to or smaller than second reference value X2 (YES in step S34), stationary terminal 90 proceeds to step S38. When stationary terminal 90 determines that second measurement value x2 is not equal to or smaller than second reference value X2 (NO in step S34), stationary terminal 90 proceeds to step S36.

In step S36, stationary terminal 90 updates the value of second reference value X2 stored in memory 96 with the value of second measurement value x2, and proceeds to step S38.

In step S38, stationary terminal 90 calculates emotion indices E1 and E2 according to equations (1) and (2). Activity value A1 used in the equations (1) and (2) is calculated according to the following equation (3), and activity value A2 used in the equations (1) and (2) is calculated according to the following equation (4).

$$A1 = x1/X1 \tag{3}$$

$$A2 = x2/X2 \tag{4}$$

In step S40, stationary terminal 90 generates evaluation information using emotion indices E1 and E2 calculated in step S38. In one implementation, stationary terminal 90 generates evaluation information by applying emotion indices E1 and E2 to map MP (FIG. 4).

In step S42, stationary terminal 90 outputs the evaluation information generated in step S40. An example of the output of the evaluation information is to display a character string constituting the evaluation information (such as "positivity of 60%") as it is. Another example is to output an image and/or audio corresponding to a character string constituting the evaluation information (such as "positivity of 60%").

In step S44, stationary terminal 90 determines whether the subject has detached wearable terminal 10. In one implementation, stationary terminal 90 determines whether the subject has detached wearable terminal 10 based on whether a sensed signal from infrared sensor 22 indicates that wearable terminal 10 has been detached from the subject.

When stationary terminal 90 determines that the subject has detached wearable terminal 10 (YES in step S44), stationary terminal 90 returns to step S10. In contrast, when stationary terminal 90 determines that the subject has not detached wearable terminal 10 (NO in step S44), stationary terminal 90 returns to step S26.

Thus, if the subject has not detached wearable terminal 10, stationary terminal 90 continues to generate and output evaluation information (steps S26 to S42). In contrast, when the subject has detached wearable terminal 10, and stationary terminal 90 detects that wearable terminal 10 is attached to a subject (YES in step S10), stationary terminal 90 obtains first reference value X1 and second reference value X2 (steps S12 to S24) and subsequently generates and outputs evaluation information (steps S26 to S42).

In the first embodiment described above, evaluation information about an expression of a subject is generated using not only a measurement value obtained as timed, as targeted, for evaluation, but also a reference value of the subject obtained in response to occurrence of a given incident. Thus, the evaluation information reflects an individual difference regarding how an emotion appears in an expression. Therefore, by using the generated evaluation information, an emotion of an individual can be accurately estimated.

While in the process described with reference to FIGS. 5 and 6, at steps S14 and S20, the reference value is obtained in a process for generating evaluation information, the reference value may be obtained as differently timed. The reference value may be obtained for each subject in advance before the above process is performed. Further, the reference value may be obtained after the measurement value is obtained.

Second Embodiment

<System Configuration>

Figure 7:
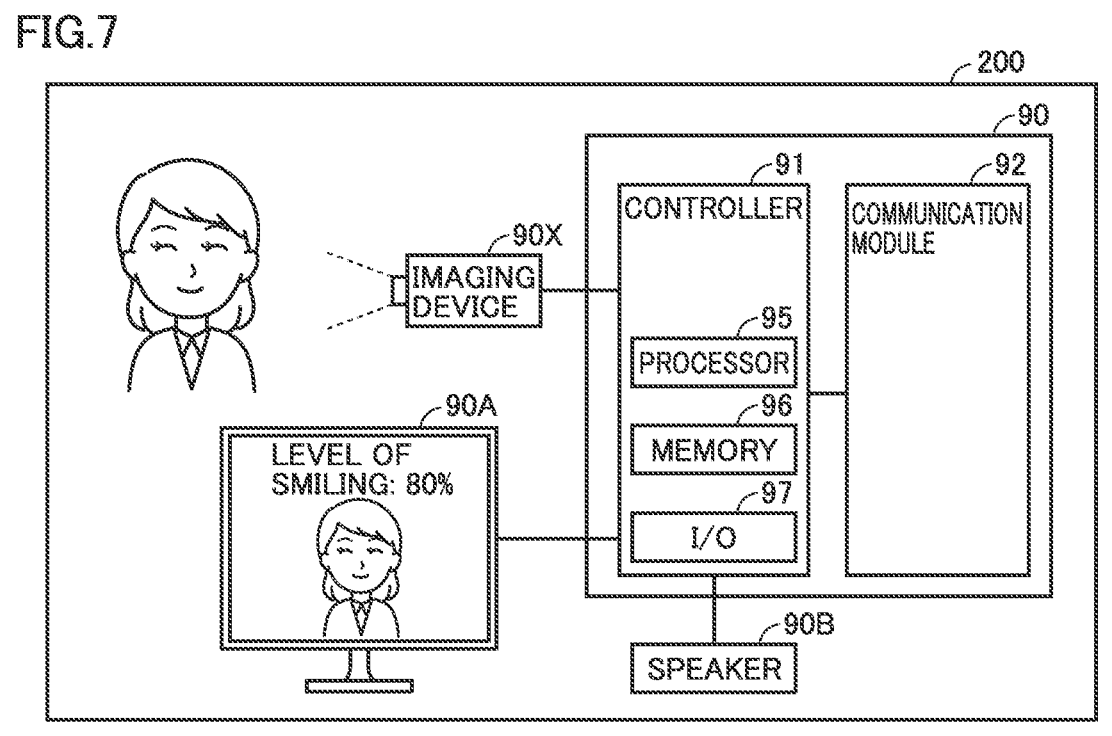

FIG. 7 is a diagram schematically showing a general configuration of an expression evaluation system according to a second embodiment. FIG. 7 shows an expression evaluation system 200, which obtains a facial image of a subject (a subject) and generates evaluation information about an expression of the subject based on a feature value obtained from the facial image. In the second embodiment, the feature value obtained from the facial image is an example of physiological information.

Expression evaluation system 200 comprises stationary terminal 90, display 90A, speaker 90B, and an imaging device 90X. Expression evaluation system 200 captures a facial image of a subject located in an imaging target range of imaging device 90X, and outputs evaluation information about an expression of the subject using the captured facial image.

In the example of FIG. 7, expression evaluation system 200 displays evaluation information on display 90A together with the facial image of the subject captured by imaging device 90X. A "level of smiling of 80%" displayed as the evaluation information corresponds to the evaluation information "positivity of 80%" shown in FIG. 4. That is, in the example of FIG. 7, "positivity" constituting evaluation information is output as "level of smiling." "Negativity" constituting evaluation information is output as a "level of disappointment." Note, however, how the evaluation information is output can be changed, as appropriate.

<Feature Value>

In the second embodiment, feature values F1 and F2 are used instead of activity values A1 and A2 in order to calculate emotion indices E1 and E2 described in the first embodiment. That is, in the second embodiment, the equations (1) and (2) are respectively changed to the following equations (5) and (6).

$$E1 = k11 \cdot F1 + k12 \cdot F2 \qquad (5)$$

$$E2 = k21 \cdot F1 + k22 \cdot F2 \qquad (6)$$

Feature value F1 is a feature value that changes as a cheek moves, and represents a feature of an expression corresponding to a positive emotion. Feature value F2 is a feature value that changes as an eyebrow moves, and represents a feature of an expression corresponding to a negative emotion. Emotion index E1 is calculated as a sum of a product of feature value F1 and coefficient k11 and a product of feature value F2 and coefficient k12. Emotion index E2 is calculated as a sum of a product of feature value F1 and coefficient k21 and a product of feature value F2 and coefficient k22.

Feature value F1 is, for example, a distance between the center of the nose and a corner of the mouth. Feature value F2 is, for example, a distance between the inner sides of the eyebrows.

<Flow of Process>

Figure 8:
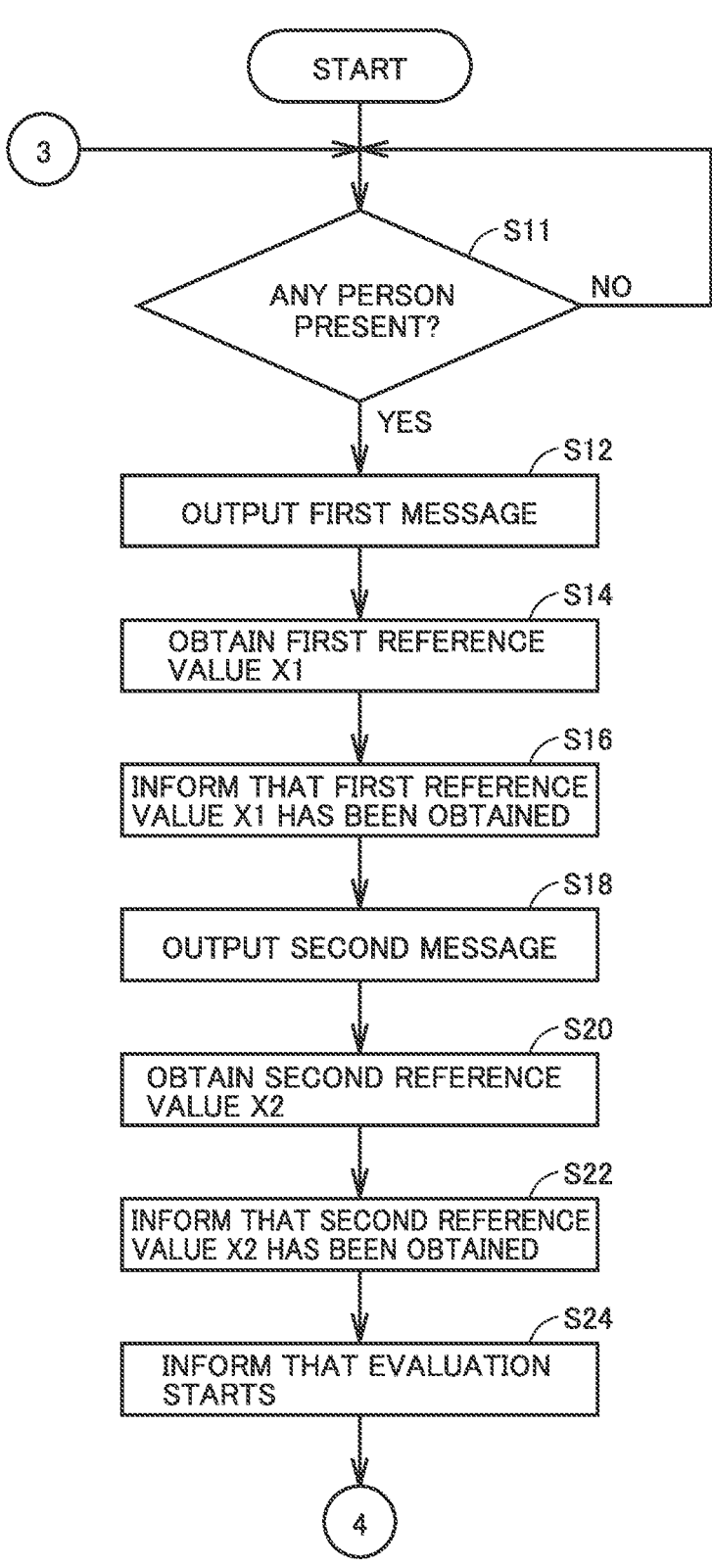
FIG. 8 is a flowchart of a process performed in an expression evaluation system 200 by stationary terminal 90 to output evaluation information (evaluation information).
Figure 9:
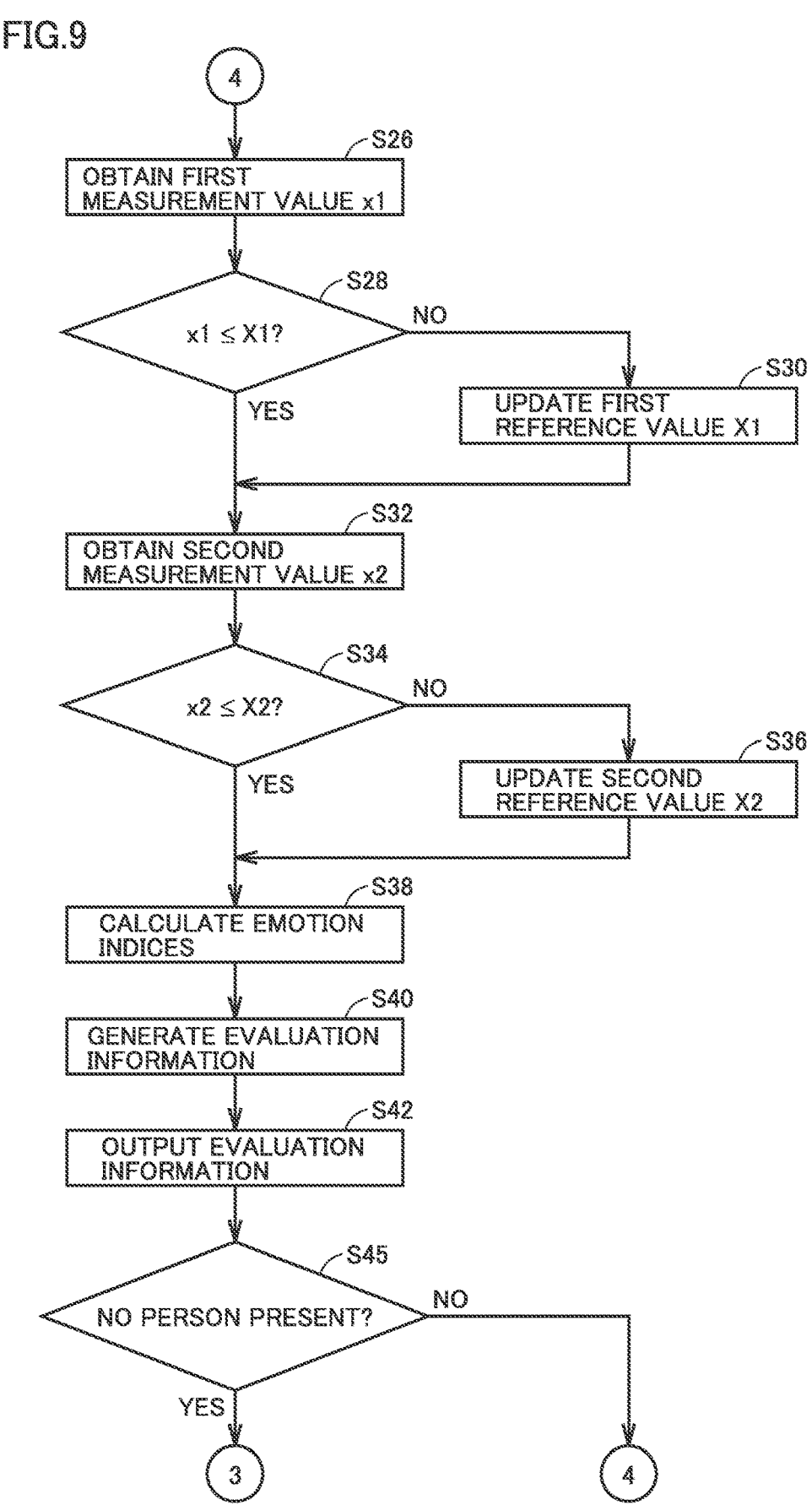
FIG. 9 is a flowchart of a process performed in expression evaluation system 200 by stationary terminal 90 to output evaluation information (evaluation information).

FIGS. 8 and 9 are a flowchart of a process performed in expression evaluation system 200 by stationary terminal 90 to output evaluation information (evaluation information). In the process shown in FIGS. 8 and 9, steps common to those shown in FIGS. 5 and 6 are identically denoted. Hereinafter, the process shown in FIGS. 8 and 9 will be described mainly with respect to points changed from the process shown in FIGS. 5 and 6.

Referring to FIG. 8, in step S11, stationary terminal 90 determines whether a person is present in the imaging target range of imaging device 90X. In one implementation, stationary terminal 90 determines whether a person is present in the imaging target range by determining whether an image captured by imaging device 90X includes a pattern determined as a human face. Recognition of a pattern determined as a human face can be implemented using a known technique, and accordingly, will not be described specifically.

Stationary terminal 90 repeats step S11 until stationary terminal 90 determines that a person is present in the imaging target range (NO in step S11). When stationary terminal 90 determines that a person is present in the imaging target range (YES in step S11), stationary terminal 90 proceeds to step S12.

In step S12, stationary terminal 90 outputs a first message (a message urging the subject to create a positive expression).

In step S14, stationary terminal 90 obtains first reference value X1. In the second embodiment, first reference value X1 is a reference value for feature value F1. In one implementation, stationary terminal 90 obtains as first reference value X1 feature value F1 in a facial image captured at a given time. Then, stationary terminal 90 stores first reference value X1 in memory 96.

In step S16, stationary terminal 90 informs that first reference value X1 has been obtained. In step S18, stationary terminal 90 outputs a second message (a message urging the subject to create a negative expression).

In step S20, stationary terminal 90 obtains second reference value X2. In the second embodiment, second reference value X2 is a reference value for feature value F2. In one implementation, stationary terminal 90 obtains as second reference value X2 feature value F2 in a facial image captured at a given time. Then, stationary terminal 90 stores second reference value X2 in memory 96.

Thereafter, stationary terminal 90 informs in step S22 that second reference value X2 has been obtained, and informs in step S24 that an evaluation of an expression of the subject starts.

Referring to FIG. 9, in step S26, stationary terminal 90 obtains first measurement value x1. In the second embodiment, first measurement value x1 is a measurement value of feature value F1. In one implementation, stationary terminal 90 obtains feature value F1 as first measurement value x1 from a facial image captured at a given time after step S24, and stores first measurement value x1 in memory 96. A "given time" is an example of timing targeted for evaluation.

In step S28, stationary terminal 90 determines whether first measurement value x1 is equal to or smaller than first reference value X1. When stationary terminal 90 determines that first measurement value x1 is equal to or smaller than first reference value X1 (YES in step S28), stationary terminal 90 proceeds to step S32. When stationary terminal 90 determines that first measurement value x1 is not equal to or smaller than first reference value X1 (NO in step S28), stationary terminal 90 proceeds to step S30.

In step S30, stationary terminal 90 updates the value of first reference value X1 stored in memory 96 with the value of first measurement value x1, and proceeds to step S32.

In step S32, stationary terminal 90 obtains second measurement value x2. In the second embodiment, second measurement value x2 is a measurement value of feature value F2. In one implementation, stationary terminal 90 obtains feature value F2 as second measurement value x2 from a facial image captured at a given time after step S24, and stores second measurement value x2 in memory 96. A "given time" is an example of timing targeted for evaluation.

In step S34, stationary terminal 90 determines whether second measurement value x2 is equal to or smaller than second reference value X2. When stationary terminal 90 determines that second measurement value x2 is equal to or smaller than second reference value X2 (YES in step S34), stationary terminal 90 proceeds to step S38. When stationary terminal 90 determines that second measurement value x2 is not equal to or smaller than second reference value X2 (NO in step S34), stationary terminal 90 proceeds to step S36.

In step S36, stationary terminal 90 updates the value of second reference value X2 stored in memory 96 with the value of second measurement value x2, and proceeds to step S38.

In step S38, stationary terminal 90 calculates emotion indices E1 and E2 according to equations (5) and (6). Feature value F1 used in the equations (5) and (6) is calculated according to the following equation (7), and feature value F2 used in the equations (5) and (6) is calculated according to the following equation (8).

$$F1 = x1 / X1 \tag{7}$$

$$F2 = x2 / X2 \tag{8}$$

In step S40, stationary terminal 90 generates evaluation information using emotion indices E1 and E2 calculated in step S38.

In step S42, stationary terminal 90 outputs the evaluation information generated in step S40.

In step S45, stationary terminal 90 determines whether there is no person in the imaging target range of imaging device 90X. In one implementation, stationary terminal 90 determines whether there is no person in the imaging target range by determining whether an image captured by imaging device 90X does not include a pattern determined as a human face.

When stationary terminal 90 determines that there is no person in the imaging target range (YES in step S45), stationary terminal 90 returns to step S11. In contrast, when stationary terminal 90 determines that a person is present in the imaging target range (NO in step S45), stationary terminal 90 returns to step S26.

Thus, when the same subject is continuously located in the imaging target range, stationary terminal 90 continues to generate and output evaluation information (steps S26 to S42). In contrast, a subject moves away from the imaging target range (YES in step S45), and thereafter when stationary terminal 90 detects that a next subject is present in the imaging target range (YES in step S11), stationary terminal 90 obtains first reference value X1 and second reference value X2 (steps S12 to S24) and subsequently generates evaluation information (steps S26 to S40).

[Specific Implementations]

Specific implementations of the presently disclosed technology will be described. It should be noted that the following description is for illustrative purposes and does not limit the presently disclosed technology to any manner for implementation.

<Evaluation of Product>

In one implementation, the presently disclosed technology is utilized for estimating a user's emotions in a series of experiences of purchasing and using a product. More specifically, the user's emotions in the experiences are estimated from evaluation information about expressions, and a result of the estimation of emotions is used as feedback information in developing products. Such an emotion estimation result can also be utilized in marketing applications such as neuroresearch.

<Evaluation of Content>

In one implementation, the presently disclosed technology is utilized for estimating emotions of a user provided with contents such as games. More specifically, emotions of the user provided with contents are estimated from evaluation information about expressions, and a result of the estimation of the emotions is used as feedback information in producing contents. More specifically, the user's impression about gaming content in degree of difficulty and/or an impression received by a user from video content may be obtained as feedback information and utilized in producing new contents.

Exemplary Variation

<Number of Types of Activity or Feature Value Used>

In the first embodiment described above, activity value A1 for a muscle in a vicinity of a cheek and activity value A2 for a muscle in a vicinity of an eyebrow are used to generate evaluation information about an expression of a subject. In the second embodiment, feature value F1 representing a feature of an expression corresponding to a positive emotion and feature value F2 representing a feature of an expression corresponding to a negative emotion are used to generate evaluation information about an expression of a subject.

An activity or feature value used for generating evaluation information about an expression of a subject is not limited to two types of such activity or feature value. One or three or more types of such activity or feature value may be used.

For example, n types of activity values A1 to An may be used to generate n types of emotion indices E1 to En according to the following expression (9), and emotion indices E1 to En may be used to generate evaluation information. In Expression (9), coefficients k11 to knn form a matrix of coefficients represented by n rows and n columns and used for generating evaluation information.

$$\begin{pmatrix} k11 & k12 & \cdots & k1n \\ k12 & k22 & & \\ \vdots & & \ddots & \\ kn1 & & & knn \end{pmatrix} \begin{pmatrix} A1 \\ A2 \\ \vdots \\ An \end{pmatrix} = \begin{pmatrix} E1 \\ E2 \\ \vdots \\ En \end{pmatrix} \tag{9}$$

<Manner of Using Reference Value>

As indicated in Equation (3) and Equation (4), an activity value used for calculating an emotion index is calculated as a ratio of a measurement value to a reference value (x1/X1 or x2/X2). Note, however, that the activity value is not required to be the ratio of the measurement value to the reference value. Insofar as the reference value is reflected in the activity value as an individual difference for each subject, the activity value may be calculated as a function of the reference value and the measurement value. Similarly, a feature value used for calculating an emotion index may also be calculated as a function of a reference value and a measurement value insofar as the reference value is reflected in the feature value as an individual difference for each subject.

<Output of Message>

In step S12, a first message for urging a subject to create a positive expression is output. In step S18, a second message urging the subject to create a negative expression is output. Outputting these messages is an example of "a given incident" that defines when first reference value X1 and second reference value X2 are obtained, and these messages are an example of content output to obtain the reference values. In response to these messages being output, first reference value X1 and second reference value X2 are obtained (steps S14 and S20).

Instead of outputting these messages, content may be output to cause a subject to create a given expression.

For example, in step S12, such contents as urging a subject to create a positive expression (video and/or audio prepared to cause the subject to laugh) may be output. In step S18, such contents as urging the subject to create a negative expression (video and/or audio prepared to discomfort or terrify the subject) may be output.

Further, the subject may not be informed of when the contents are output. That is, when stationary terminal 90 outputs the content(s), stationary terminal 90 may generate first reference value X1 and second reference value X2 without notifying the subject accordingly. Thus, first reference value X1 and second reference value X2 can be obtained based on a positive expression and a negative expression, respectively, created by the subject unconsciously.

<Detection of New Subject>

According to the first embodiment, in step S44, whether a subject is still wearing wearable terminal 10 is determined after first and second reference values X1 and X2 are obtained in steps S14 and S20, respectively. And once it is determined that the subject has detached wearable terminal 10, then, after it is determined that a subject has again detached wearable terminal 10, first and second reference values X1 and X2 are again obtained in steps S14 and S20, respectively.

According to the second embodiment, in step S45, whether a subject is still located in the imaging target range of imaging device 90X is determined after first and second reference values X1 and X2 are obtained in steps S14 and S20, respectively. And once it is determined that the subject is no longer located in the imaging target range of imaging device 90X, then, after it is determined that a subject is again located in the imaging target range of imaging device 90X, first and second reference values X1 and X2 are again obtained in steps S14 and S20, respectively.

According to the above-described control, when a new subject is detected as a target for evaluating an expression, new first and second reference values X1 and X2 are obtained. As a result, even when a subject is changed, first and second reference values X1 and X2 can be obtained for each subject.

In this sense, step S10 is an example of control for detecting a new subject. Further, step S11 is another example of control for detecting a new subject. And first and second reference values X1 and X2 are obtained in steps S14 and S20, respectively, in response to a new subject being detected.

A new subject may be detected in any manner other than wearable terminal 10 being attached, as described in the first embodiment, and a person being detected in the imaging target range, as described in the second embodiment. For example, a new subject may be sensed by a human sensor, or may be detected in response to a dedicated button being pressed.

Further, while in the above embodiments an example in which a reference value is updated when a measurement value is higher than the reference value has been described, the present invention is not limited thereto, and an example in which the reference value is updated when the measurement value is lower than the reference value is also encompassed depending on the target to be measured.

For example, when a frowning expression is evaluated by a myoelectric potential in a vicinity of an eyebrow, a more frowning expression results in a larger measurement value, and accordingly, it is appropriate to update the reference value when the measurement value exceeds the reference value. In this case, the measurement value exceeding the reference value may be one example of a measurement result exceeding a reference.

In contrast, when the same frowning expression is captured by a distance between the inner sides of the eyebrows, a more frowning expression results in a smaller measurement value, and accordingly, it is appropriate to update the reference value when the measurement value is below the reference value. In this case, the measurement value below the reference value may be an example of a measurement result exceeding a reference.

The term "reference value" is used as an example of a reference for a subject, and the reference may be represented in a manner other than a value. Further, the term "measurement value" is used as an example of a measurement result about a subject, and the measurement result may be represented in a manner other than a value. That is, the reference and measurement result in this paragraph may be represented in a manner other than a value, such as image information. And when the reference and the measurement result are used to generate information about an expression of a subject, the information may be generated by comparing images or the like.

Aspects

It is understood by those skilled in the art that the above-described exemplary embodiments are specific examples of the following aspects:

(Clause 1) An evaluation method according to an aspect is a method for evaluating a facial expression of a subject, and may comprises: obtaining a reference value for physiological information of a facial area of the subject; obtaining a measurement value of the physiological information of the facial area of the subject at a targeted timing for evaluation; generating evaluation information about a facial expression of the subject using the reference value and the measurement value; and outputting the evaluation information.

According to the evaluation method according to clause 1, a technique for accurately estimating an emotion of an individual is provided.

(Clause 2) The evaluation method according to Clause 1, wherein a reference value and a measurement value may respectively be obtained as the reference for and measurement result of the physiological information of the facial area of the subject.

According to the evaluation method according to Clause 2, the evaluation information can be easily generated.

(Clause 3) The evaluation method according to Clause 2, wherein the generating evaluation information about a facial expression of the subject may include calculating the evaluation information using a ratio of the measurement value to the reference value.

According to the evaluation method according to Clause 3, the evaluation information can be generated more easily.

(Clause 4) The evaluation method according to Clause 2 or 3, further comprising updating the reference value by replacing the reference value with the measurement value when the measurement value exceeds the reference value.

According to the evaluation method according to Clause 4, the emotion of the individual can be more accurately estimated by the evaluation information.

(Clause 5) The evaluation method according to any one of Clauses 2 to 4, wherein the reference value and the measurement value may each include one or more types of feature values of a face of the subject that are obtained from a facial image of the subject.

According to the evaluation method according to Clause 5, the emotion of the individual can be more accurately estimated by the evaluation information.

(Clause 6) The evaluation method according to Clause 5, wherein the one or more types of feature values may include at least one of a first feature value changing as a cheek moves and a second feature value changing as two eyebrows move.

According to the evaluation method according to Clause 6, the emotion of the individual can be more accurately estimated by the evaluation information.

(Clause 7) The evaluation method according to Clause 6, wherein the first feature value may be a distance between a nose and a corner of a mouth.

According to the evaluation method according to Clause 7, the evaluation information can be easily generated.

(Clause 8) The evaluation method according to Clause 6 or 7, wherein the second feature value may be a distance between the two eyebrows.

According to the evaluation method according to Clause 8, the evaluation information can be easily generated.

(Clause 9) The evaluation method according to any one of Clauses 1 to 8, wherein the physiological information of the facial area of the subject is obtained from a myoelectric potential signal of a facial muscle of the subject.

According to the evaluation method according to Clause 9, the emotion of the individual can be more accurately estimated by the evaluation information.

(Clause 10) The evaluation method according to Clause 9, wherein the facial muscle may include at least one of a muscle in a vicinity of a cheek and a muscle in a vicinity of an eyebrow.

According to the evaluation method according to Clause 10, the emotion of the individual can be more accurately estimated by the evaluation information.

(Clause 11) The evaluation method according to any one of Clauses 1 to 10, wherein the physiological information of the facial area of the subject is obtained from a facial image of the subject.

According to the evaluation method according to Clause 11, the emotion of the individual can be more accurately estimated by the evaluation information.

(Clause 12) The evaluation method according to any one of Clauses 1 to 11, that may further comprise outputting content for obtaining the reference, wherein the obtaining a reference is performed in response to the content being output.

According to the evaluation method according to Clause 12, the evaluation information can be easily generated.

(Clause 13) The evaluation method according to any one of Clauses 1 to 12, that may further comprise detecting a new subject as a target for evaluating a facial expression, wherein the obtaining a reference is performed in response to the new subject being detected.

According to the evaluation method according to Clause 13, even when a subject is changed, a reference value can be obtained for each subject.

(Clause 14) An evaluation system according to an aspect is a system for evaluating a facial expression of a subject and may comprise a processor and an interface for obtaining physiological information of a facial area of the subject, and the processor may be configured to generate evaluation information about a facial expression of the subject using a reference for the physiological information of the facial area of the subject and a measurement result of the physiological information of the facial area of the subject obtained at a targeted timing for evaluation, and output the evaluation information.

According to the evaluation system according to Clause 14, a technique for accurately estimating an emotion of an individual is provided.

(Clause 15) A non-transitory computer-readable storage medium according to an aspect is a medium storing a program for causing an evaluation of a facial expression of a subject and may be executed by a processor of a computer to cause the computer to: obtain a reference for physiological information of a facial area of the subject; obtain a measurement result of the physiological information of the facial area of the subject at a targeted timing for evaluation; generate evaluation information about the facial expression of the subject using the reference and the measurement result; and output the evaluation information.

According to the program according to Clause 15, a technique for accurately estimating an emotion of an individual is provided.

It should be understood that the presently disclosed embodiments are illustrative and non-restrictive in any respect. The scope of the present disclosure is defined by the terms of the claims, rather than the above description of the embodiments, and is intended to include any modifications within the meaning and scope equivalent to the terms of the claims. It is also contemplated that each technique in the embodiments can be implemented alone or in combination with other techniques in the embodiments as much as possible as necessary.

REFERENCE SIGNS LIST 1 sensor unit, 2 signal processing circuit, 3, 91 controller, 4, 92 communication module, 5 battery, 6 housing, 10 wearable terminal, 10A first arm, 10B second arm, 11 first myoelectric potential sensor, 12 second myoelectric potential sensor, 14, 24, AR11, AR21 region, 21, 90B speaker, 22 infrared sensor, 31, 95 processor, 32, 96 memory, 33, 97 I/O port, 90 stationary terminal, 90A display, 90X imaging device, 100, 200 expression evaluation system, 111, 121 working electrode, 112, 122 reference electrode, 141, 142, 161, 162 line, 151, 152, 171, 172 pad.

The invention claimed is:

1. A method for evaluating a facial expression of a subject, comprising:
obtaining a reference for physiological information of a facial area of the subject;
obtaining a measurement result of the physiological information of the facial area of the subject at a targeted timing for evaluation;

generating evaluation information about a facial expression of the subject using the reference and the measurement result; and outputting the evaluation information wherein a reference value is obtained as the reference for the physiological information of the facial area of the subject and a measurement value is obtained as the measurement result of the physiological information of the facial area of the subject, and wherein the method further comprises updating the reference value by replacing the reference value with the measurement value when the measurement value exceeds the reference value.

2. The method according to claim 1, wherein the generating evaluation information about a facial expression of the subject includes calculating the evaluation information using a ratio of the measurement value to the reference value.

3. The method according to claim 1, wherein the reference value and the measurement value each include one or more types of feature values of a face of the subject that are obtained from a facial image of the subject.

4. The method according to claim 3, wherein the one or more types of feature values include at least one of a first feature value changing as a cheek moves and a second feature value changing as two eyebrows move.

5. The method according to claim 4, wherein the first feature value is a distance between a nose and a corner of a mouth.

6. The method according to claim 4, wherein the second feature value is a distance between the two eyebrows.

7. The method according to claim 1, wherein the physiological information of the facial area of the subject is obtained from a myoelectric potential signal of a facial muscle of the subject.

8. The method according to claim 7, wherein the facial muscle includes at least one of a muscle in a vicinity of a cheek and a muscle in a vicinity of an eyebrow.

9. The method according to claim 1, wherein the physiological information of the facial area of the subject is obtained from a facial image of the subject.

10. The method according to claim 1, further comprising outputting content for obtaining the reference, wherein the obtaining a reference is performed in response to the content being output.

11. The method according to claim 1, further comprising detecting a new subject as a target for evaluating a facial expression, wherein the obtaining a reference is performed in response to the new subject being detected.

12. A system for evaluating a facial expression of a subject, comprising:

a processor; and an interface that obtains physiological information of a facial area of the subject, wherein the processor generates evaluation information about a facial expression of the subject using a reference for the physiological information of the facial area of the subject and a measurement result of the physiological information of the facial area of the subject obtained at a targeted timing for evaluation, and outputs the evaluation information, wherein a reference value is obtained as the reference for the physiological information of the facial area of the subject and a measurement value is obtained as the measurement result of the physiological information of the facial area of the subject, and wherein the processor updates the reference value by replacing the reference value with the measurement value when the measurement value exceeds the reference value.

13. A non-transitory computer-readable storage medium storing a program for causing an evaluation of a facial expression of a subject, the program being executed by a processor of a computer to cause the computer to perform:

obtaining a reference for physiological information of a facial area of the subject;

obtaining a measurement result of the physiological information of the facial area of the subject at a targeted timing for evaluation;

generating evaluation information about a facial expression of the subject using the reference and the measurement result; and outputting the evaluation information, wherein a reference value is obtained as the reference for the physiological information of the facial area of the subject and a measurement value is obtained as the measurement result of the physiological information of the facial area of the subject, and wherein the program further causes the computer to perform updating the reference value by replacing the reference value with the measurement value when the measurement value exceeds the reference value.

* * * * *